Dec. 3, 1935. R. L. BYRUM Plant Pat. 155
ROSE
Filed Jan. 9, 1935
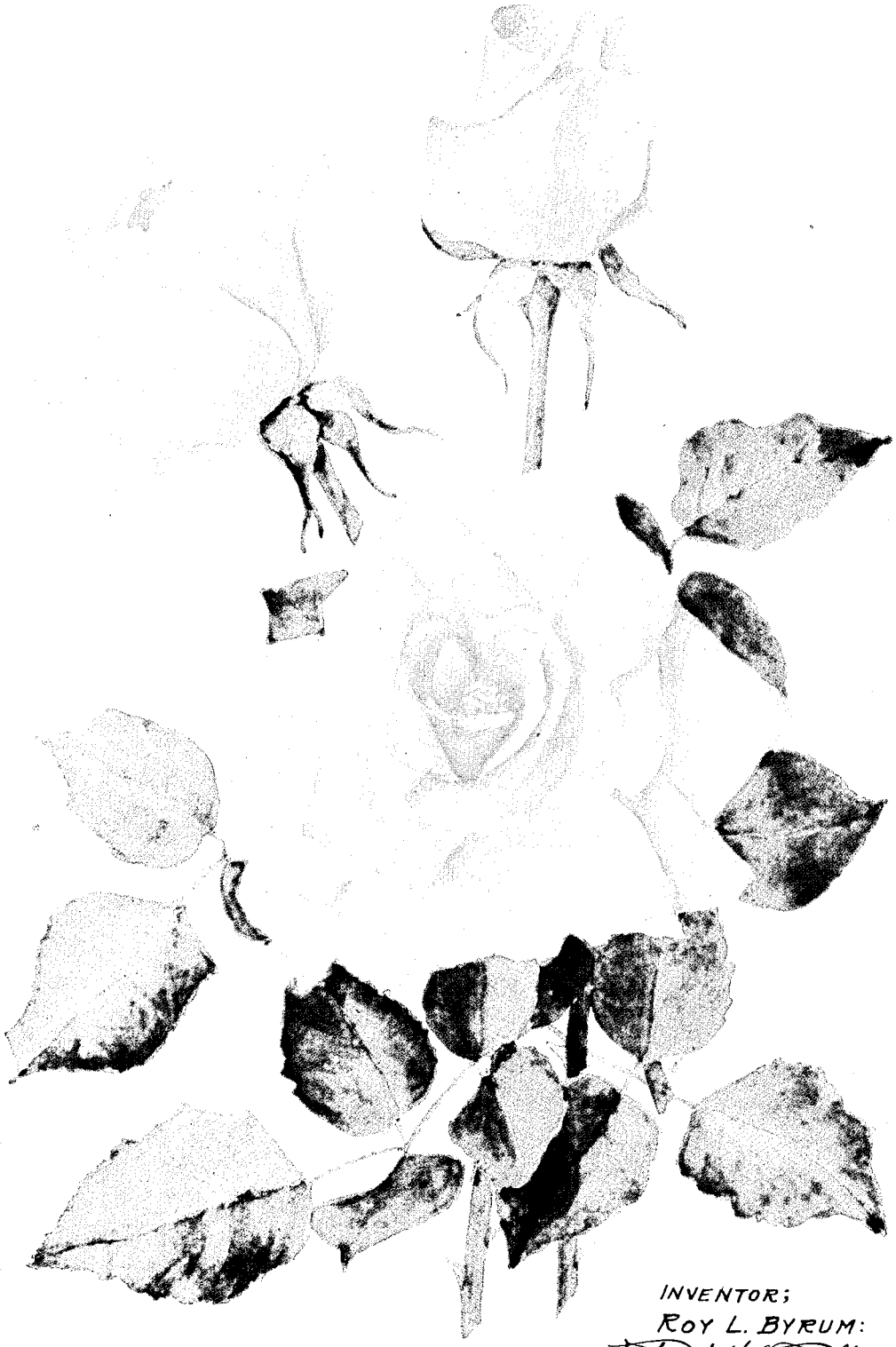
INVENTOR;
ROY L. BYRUM:
BY Robert W. Caudle
ATTORNEY.

Patented Dec. 3, 1935 Plant Pat. 155

UNITED STATES PATENT OFFICE

155

ROSE

Roy L. Byrum, Richmond, Ind., assignor to Joseph H. Hill Company, Richmond, Ind., a corporation of Indiana Application January 9, 1935, Serial No. 1,042

1 Claim. (Cl. 47—61)

I developed this new rose by crossing a Sweet Adeline rose, which is shown in Plant Patent No. 6, with a Joanna Hill rose, which is registered but not patented, producing a hybrid tea-rose of the ever blooming type, which I will now describe in detail.

*Generation.*—I produced this new rose by hybridization, employing a Sweet Adeline rose as the male parent and a Joanna Hill rose as the female parent. The combination of said two varieties of roses was obtained as follows: In the month of March, of the year 1930, I collected pollen from the stamens of said male parent and deposited it on the stigmas which conducted it into the ovaries of the female parent. From the product of the above I obtained roses of three distinct new varieties, each of which presented certain new and distinct features, one of which is the subject of this application, and it is shown, as nearly as possible, in the accompanying illustration, as in three stages of development.

One of said roses, which is the subject of this application, was produced by hybridization and close personal supervision, whereby the features, herein shown and described, have become fixed as a new variety of roses, which features I will now describe as fully and as clearly as seems possible.

The discovery, development and completion of this rose, as a new variety, was made in the greenhouses of the Joseph H. Hill Company, in Richmond, Indiana, and it is believed that its characteristics, as a new variety, became fixed and permanent in December, 1934, and soon thereafter the following description was made from flowers grown in said greenhouses of the Joseph H. Hill Company, Richmond, Indiana.

*Buds.*—The buds of this new variety of roses are very large, pointed, and open well.

The color of the buds, before the calyx bursts, is considerably darker than "ochraceous-salmon" (Plate XV, Ridgway color chart). As the calyx opens the color of the bud is almost identical with said "ochraceous-salmon" in color, but they gradually continue to become lighter than "ochraceous-salmon" until they are fully opened, after which no change in color is noticeable.

*Flowers.*—The flowers are double, firm, full, and graceful in their appearance. There are usually twenty-eight to thirty-five petals to each flower. When the flower is first opened out the shape thereof is round, and tapers outwardly from its central portion, but thereafter it gradually flattens out and becomes slightly oval. The upper faces of the petals are glossy, and their under sides appear the same.

The color of the flowers, taken as a whole, and when the viewer is located at a distance therefrom, appears as a single yellow unit, with the color thereof, as an entirety, appearing similar to the Joanna Hill rose, but slightly darker, similar to "apricot yellow", shown on plate IV of Ridgway color chart. The outer portion of the petals is almost white, with a very light tinge of color similar to "seashell pink" shown on plate XIV of Ridgway color chart, but it gradually becomes darker as it approaches the inner portion of the petal. The color of the petals gradually becomes lighter as they develop. The petals are soft and velvety; and the blooms retain their fully open shape and their beauty of foliage for a long period of time. This rose is of the type designated as continuous blooming. When the blooms are cut from the stem, a new crop develops in thirty-five to forty days thereafter.

*Stamens.*—The stamens are numerous and of uneven lengths, with buff anthers, and white, but not very prominent filaments.

*Pistils.*—The pistils are numerous and of even length; the stigmas are white and prominent.

*Foliage.*—The foliage is abundant and is composed of compound leaves, usually of three leaflets near the flower and five to seven further down the stem. The leaflets are almost round, or oval, the upper surface of the leaves are dark-green and the lower surfaces are a light green, with the new growth much lighter.

*Bush.*—The bush, as a whole, is of a vigorous and quick growth, with numerous branches. The wood is stiff and not easily broken, and it is very compact. The stems grow to a length of thirty to thirty-six inches. The peduncles, above the upper leaves, are long, strong, heavy, green in color, and free from thorns.

*Aroma.*—The aroma of this rose is mild and persistent, and of a tea-fragrance which persists throughout the usefulness of the bloom.

What I claim, and desire to secure by Letters Patent of the United States, is—

A new variety of roses, characterized by its large bloom, the predominant dark yellow color of its bloom and the color combination thereof, the exceptional height of the bush as an entirety, its vigor and quickness of growth and development, the mild and persistent tea-fragrance of the bloom, and its display beauty as an entirety.

ROY L. BYRUM.